United States Patent
Toivanen et al.

(10) Patent No.: US 8,188,039 B2
(45) Date of Patent: May 29, 2012

(54) VEGF-D MUTANTS AND THEIR USE

(75) Inventors: Pyry Toivanen, Kuopio (FI); Kari Juhani Airenne, Kuopio (FI); Seppo Yla-Herttuala, Kuopio (FI)

(73) Assignee: Ark Therapeutics Group, plc, London (GB)

( * ) Notice: Subject to any disclaimer, the term of this patent is extended or adjusted under 35 U.S.C. 154(b) by 124 days.

(21) Appl. No.: 12/599,294

(22) PCT Filed: Jun. 2, 2008

(86) PCT No.: PCT/GB2008/001873
§ 371 (c)(1), (2), (4) Date: Aug. 20, 2010

(87) PCT Pub. No.: WO2008/146023
PCT Pub. Date: Dec. 4, 2008

(65) Prior Publication Data
US 2011/0144013 A1 Jun. 16, 2011

(30) Foreign Application Priority Data
May 31, 2007 (GB) .................................. 0710457.3

(51) Int. Cl.
*A61K 388/18* (2006.01)
*C07K 14/475* (2006.01)
*C12N 15/18* (2006.01)

(52) U.S. Cl. ........ 514/8.1; 435/69.1; 536/23.5; 530/399

(58) Field of Classification Search ................... None
See application file for complete search history.

(56) References Cited

PUBLICATIONS

Achen, M. G. et al. "Vascular endothelial growth factor D (VEGF-D) is a ligand for the tyrosine VEGF receptor 2 (FLK1) receptor 3 (FLT4)" *Proceedings of the National Academy of Sciences of USA, National Academy of Science*, Washington DC, 1998, pp. 548-553, vol. 95, No. 2.

Claffey, K. P. et al. "Structural Requirements for dimerization, glycosylation, secretion, and biological function of VPF/VGF" *Biochimica at biophysics acta. Biomembranes*, Amsterdam, NL, 1995, pp. 1-09, vol. 1246.

Kirkin, V. et al. "Characterization of indolinones which preferentially inhibit VEGF-C and VEGF-D induced activation of VEGF-3 rather than VEGFR-2" *European Journal of Biochemistry, Berlin*, 2001, pp. 5530-5540, vol. 268.

McColl, B. K. et al. "Proprotein convertases promote processing of VEGF-D a critical step for binding the angiogenic receptor VEGFR-2" *The FASEB Journal: Official Publication of the Federation of American Societies for Experimental Biology*, 2007, pp. 1088-1098, vol. 21, No. 4.

Rissanen, T. T. et al. "VEGF-D is the strongest angiogenic and lymphangiogenic effector among VEGFs delivered into skeletal muscle via adenoviruses" *Circulation Research*, 2003, pp. 1098-1106, vol. 92, No. 10.

Roy of al, "Biology of vascular endothelial growth factors" *FEBS Letters, Elsevier, Amsterdam, NL*, pp. 2879-2887, vol. 580, No. 12.

Stacker, S. et al. "Biosynthesis of vascular endothelial growth factor-D involves generates non-covalent homodimers" *Journal of Biological Chemistry, American Society of Biolochemical Biologists, Birmingham*, 1999, pp. 32127-32136, vol. 274 No. 45.

Walsh, T. P. et al. "Computer modelling of the receptor-binding domains of VEGF and PIGF" *Protein Engineering, Oxford University Press, Surrey*, 1997, pp. 389-398, vol. 10, No. 4.

*Primary Examiner* — Christine J Saoud
(74) *Attorney, Agent, or Firm* — Pharmaceutical Patent Attorneys, LLC

(57) ABSTRACT

The present invention is a VEGF-D protein, containing one or more amino acid mutations at the dimer interface, and their use in therapy, particularly in the promotion of angiogenesis.

8 Claims, 2 Drawing Sheets

Figure 1

```
                            10              20              30              40
VEGF-D^ΔNΔC  1  F Y D I E T L K V I D E E W Q R T Q C S P R E T C V E V A S E L G K S T N T F F
VEGF-A      39  . . . . E V V K F M D . V Y Q R S Y C H P I E T L V D I F Q E Y P D E I E Y I F
VEGF-B      34  . . . . K V V S W I D . V Y T R A T C Q P R E V V V P L T V E L M G T V A K Q L
VEGF-C     117  . . . . E I L K S I D N E W R K T Q C M P R E V C I D V G K E F G V A T N T F F
VEGF-D      97  . . . . E T L K V I D E E W Q R T Q C S P R E T C V E V A S E L G K S T N T F F
PlGF        39  . . . . E V V P F Q E . V W G R S Y C R A L E R L V D V V S E Y P S E V H M F 50              60              70              80
VEGF-D^ΔNΔC 41  K P P C V N V F R C G G C C N E E S L I C M N T S T S Y I S K Q L F E I S V P L
VEGF-A      74  K P S C V P L M R C G G C C N D E G L E C V P T E E S N I T M Q I M R I K P H .
VEGF-B      69  V P S C V T V Q R C G G C C P D D G L E C V P T G Q H Q V R M Q I L M I R Y P .
VEGF-C     153  K P P C V S V Y R C G G C C N S E G L Q C M N T S T S Y L S K T L F E I T V P L
VEGF-D     133  K P P C V N V F R C G G C C N E E S L I C M N T S T S Y I S K Q L F E I S V P L
PlGF        74  S P S C V S L L R C T G C C G D E N L H C V P V E T A N V T M Q L L K I R S G .

90             100
VEGF-D^ΔNΔC 81  T S V P E L V P V K V A N H T G C K C L P T A P R H P Y S
VEGF-A     113  . Q G Q H I G E M S F L Q H N K C E C R P K . . . . . .
VEGF-B     108  . S S Q . L G E M S L E E H S Q C E C R P K . . . . . .
VEGF-C     193  S Q G P K P V T I S F A N H T S C R C M S K . . . . . .
VEGF-D     173  T S V P E L V P V K V A N H T G C K C L P T . . . . . .
PlGF       113  . D R P S Y V E L T F S Q H V R C E C R P L . . . . . .
```

VEGF-D MUTANTS AND THEIR USE

This application is a National Stage Application of International Application Number PCT/GB2008/001873, filed Jun. 2, 2008; which claims priority to Great Britain Application No. 0710457.3, filed May 31, 2007, which is incorporated herein by reference in its entirety.

FIELD OF THE INVENTION

This invention relates to modifications of VEGF-D, which increase its activity at the VEGF receptor, and their use in therapy.

BACKGROUND OF THE INVENTION

Vascular endothelial growth factors (VEGFs) are considered as key growth factors inducing angiogenesis and lymphangiogenesis during embryogenesis, as well as maintaining vasculature during adulthood. Their abnormal expression is also found on several pathological conditions such as cancer and retinopathies. VEGF-A belongs to the larger family of related growth factors including VEGF-B, -C, -D and placental growth factor PlGF as well as Orf virus derived VEGF-E proteins and multiple homologues from snake venoms. Endogenous VEGF protein family members in humans exist as several isoforms either as a result of alternative splicing of the mRNAs or due to proteolytic processing. The angiogenic effects of these variants vary considerably due to their differing specificities and affinities to three main VEGF receptors, co-receptors such as neuropilins, heparan sulphate proteoglycans and other components of the extracellular matrix.

VEGFR-2 is the most important receptor regulating angiogenesis and it is mainly expressed on endothelial cells. Mammalian VEGFR-2 ligands include VEGF-A, VEGF-C and VEGF-D. In addition to VEGFR-2 VEGF-C and -D are ligands of VEGFR-3 which is the receptor mediating lymphangiogenesis and partakes therefore in the formation of lymphatic vasculature. VEGF-A binds also to VEGFR-1 which functions during embryogenesis mainly as a non-signalling decoy receptor. In adult organism this receptor is known to mediate migration of inflammatory cells such as macrophages and monocytes but its role in angiogenesis is still controversial.

Due to their importance as angiogenic regulators, the VEGF family members have been suggested as potential therapeutics in order to adjust the angiogenic processes in different pathological conditions (Ylä-Herttuala 2003). In vivo studies have been done to induce angiogenesis by introducing VEGFs to tissues either directly as recombinant proteins or using gene therapy vectors (Markkanen 2005). The findings from several studies have shown that VEGF family members have strong angiogenic activity in vivo and they are potentially useful therapeutics for conditions like lower limb ischemia and coronary artery disease. Out of these factors, the mature form of VEGF-D (VEGF-D$^{\Delta N\Delta C}$, see below) and VEGF-A have been found to be the most promising to induce therapeutic angiogenesis.

VEGFs share structural similarity with platelet-derived growth factors (PDGFs) and together they are classified as VEGF/PDGF family, which belongs to bigger cysteine knot growth factor superfamily. Family members share a cysteine knot motif which is found in many extracellular proteins and is conserved among numerous species. Characteristic to cysteine knot proteins is that they contain a conserved structure of antiparallel β-sheets connected by three disulfide bonds. Typically cysteine knot growth factors form dimers which in the case of VEGF/PDGF family are often linked by intersubunit disulfide bonds.

VEGF receptors belong to receptor protein tyrosine kinases which are activated by dimerization. For VEGFR activation, dimerization of the ligand is indispensable. One VEGF-A dimer binds from its both poles to two separate receptor monomers, inducing receptor dimerization and consequently intracellular tyrosine kinase activity. Based on the several experimentally solved 3D structures of VEGF family members either free or as a complex with VEGF receptor, they all have closely similar tertiary structures and so probably induce receptor activation by similar mechanisms.

In the VEGF family, VEGF-C and VEGF-D can be subdivided into their own subfamily, which is reflected by their higher primary sequence structure similarity as compared to other VEGFs. There are several characterising features including: 1) they are the only VEGFs that bind to VEGFR-3, the lymphangiogenesis mediating receptor; 2) by contrast to VEGF-A, -B and PLGF, VEGF-C and VEGF-D are expressed as long preproteins. These forms have poor receptor-binding affinities and, in order to be converted to more active growth factors, VEGF-C and VEGF-D are proteolytically processed both from their N-terminal and C-terminal ends; 3) in contrast to other members of the family, the mature proteolytically processed form of VEGF-D, VEGF-D$^{\Delta N\Delta C}$, has been found to exist mainly as a non-covalently bound dimer or monomer and only in small degree as a covalently bound disulfide bond-linked dimer. These studies have also shown that the monomeric fraction of VEGF-D$^{\Delta N\Delta C}$ is also only very weakly active when compared to the dimeric fraction. The mainly non-covalent nature of the dimers is somewhat surprising, since the cysteine residues that form the intersubunit linkage in other VEGF family growth factors are conserved in the VEGF-D protein.

The cysteines of VEGF-A involved in cysteine knot structure have been mutagenized in previous studies to investigate their importance for the structure and function of the protein. The intersubunit disulfide bonds have been found to be necessary for its biological function, as VEGF-A where these cysteines have been mutated to alanines has lost its biological activity. A VEGF-C mutant where one of the conserved cysteines (Cys156) has been converted to serine has completely lost its VEGFR-2 activation ability, but is still able to activate VEGFR-3. Both mature forms of VEGF-C and VEGF-D also contain an unpaired cysteine residue located close to the proposed intersubunit disulfide bonds forming cysteine residues. The pvf-1 gene from *C. elegans* has been recently shown to code for a VEGF/PDGF homolog that activates human VEGFR-1 and -2 and is also only partially covalently bound dimer. This protein also has a unpaired cysteine on the dimer interface, like VEGF-C and VEGF-D.

SUMMARY OF THE INVENTION

The present invention is based on a study in which both the cysteines responsible for the intersubunit disulfide bridge formation in other VEGFs, and the unpaired interface cysteine residue of VEGF-D were each mutagenized separately to alanine, using as a protein scaffold the mature VEGF-D form VEGF-D$^{\Delta N\Delta C}$ (Achen 1998, Stacker 1999). VEGF-D is proteolytically processed in order to be more active, but this proteolytically processed form exists mainly as a non-covalently bound dimer or a monomer. It was found that an increase in covalent dimerization of mature VEGF-D, VEGF-D$^{\Delta N\Delta C}$, can be achieved by altering the dimer-forming interface of VEGF-D by mutagenesis. Also, it was found that the replacement of Cys25 with a variety of different amino acids in the VEGF-D$^{\Delta N \Delta C}$ protein increased the formation of covalent dimer and also markedly increased the activity of the protein at the VEGF receptors. The present invention is based on the realization that, for VEGF receptor activation, covalent dimerisation of the VEGF ligand is favorable. The present invention is therefore a VEGF-D protein, which is modified in that one or more amino acids has been replaced by another amino acid, such that the dimer interface is altered

DESCRIPTION OF THE DRAWINGS

FIG. 1 shows alignment of VEGF-D$^{\Delta N \Delta C}$ amino acid sequence with VEGF homology domain sequences of mammalian VEGF family members. Cysteine residues and the mutated cysteine residues in the VEGF-D$^{\Delta N \Delta C}$ sequence are highlighted.

Figure 2:
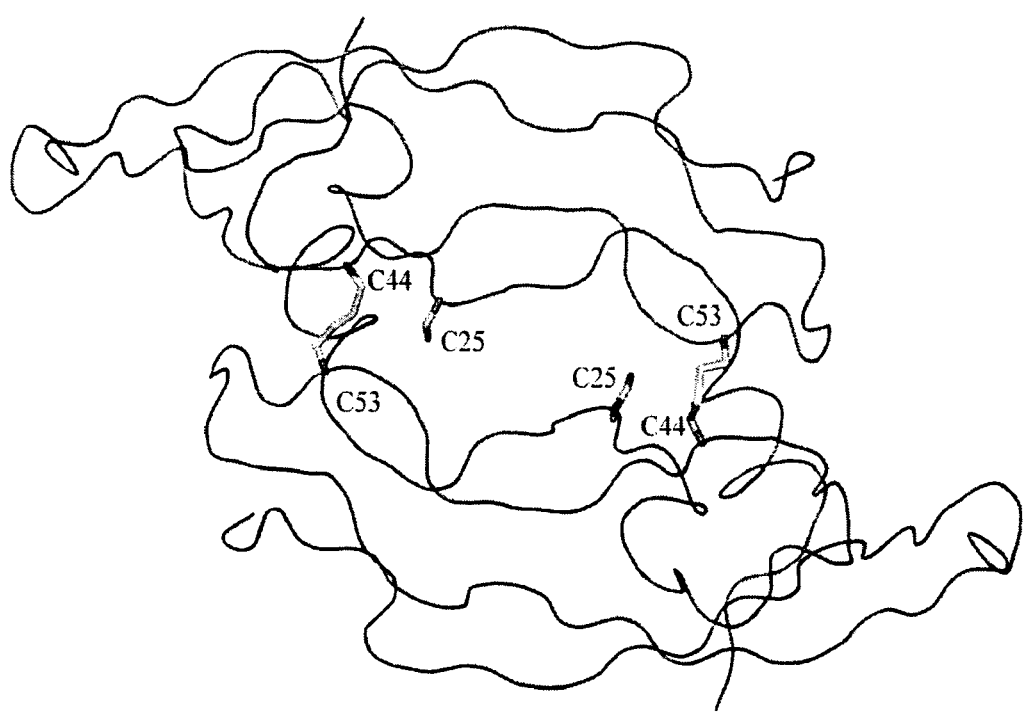

The sequence of VEGF-D$^{\Delta N \Delta C}$ is provided in SEQ ID NO: 1. The sequence of VEGF-A is provided in SEQ ID NO: 2. The sequence of VEGF-B is provided in SEQ ID NO: 3. The sequence of VEGF-C is provided in SEQ ID NO: 4. The sequence of VEGF-D is provided in SEQ ID NO: 5. The sequence of PlGF is provided in SEQ ID NO: 6.

FIG. 2 shows the locations of mutated cysteine residues on the homology model of VEGF-D$^{\Delta N \Delta C}$. The mutated cysteine amino acid residues are named according to their positions in the VEGF-D$^{\Delta N \Delta C}$ sequence.

DESCRIPTION OF PREFERRED EMBODIMENTS

The present invention is a VEGF-D protein which is modified in that one or more amino acids has been replaced by another amino acid, such that the dimer interface is altered. This definition encompasses any amino acid mutation that affects the dimer interface of the VEGF-D protein, ie. an amino acid that is important for VEGF-D dimer formation. The dimer interface is the area on the VEGF-D protein that is bonded to another VEGF-D protein, when dimerised. Preferably, the conformation of the dimer interface is altered. This may occur due to the mutation affecting the protein three-dimensional structure. The amino acid that is mutated may be an amino acid that is bonded to another amino acid, when the protein is dimerised. An example of an amino acid that can alter the dimer interface is the Cys25 of VEGF-D$^{\Delta N \Delta C}$.

A VEGF-D protein of the invention contains mutations such that the dimerisation properties of the protein are altered compared to the wild-type protein. Preferably, the VEGF-D mutants of the invention have a higher dimer to monomer ratio than the wild-type VEGF-D. Therefore, in the present invention, the VEGF-D protein may exist as a monomer, a dimer, or a mixture thereof. Preferably, the VEGF-D protein exits substantially as a dimer.

The sequence of proteolytically processed VEGF-D, VEGF-D$^{\Delta N \Delta C}$, is given as SEQ ID NO: 1. In a preferred embodiment, the present invention comprises a VEGF-D$^{\Delta N \Delta C}$ (SEQ ID NO: 1) protein, wherein one or more of the Cys residues has been replaced by another amino acid. This mutation may increase the dimer to monomer ratio compared to the wild-type VEGF-D$^{\Delta N \Delta C}$. In a preferred embodiment, amino acid 25 of that sequence (Cys25) has been replaced by another amino acid. Preferably, the amino acid is selected from Leu, Ile, Val, Ala, Ser, Phe, Trp and Asn. More preferably, the amino acid is selected from Leu, Ile and Val.

A VEGF-D protein of the invention, or an expression vector including a nucleotide sequence encoding a VEGF protein of the invention, may be used for the manufacture of a medicament for the promotion of angiogenesis. The promotion of angiogenesis may be useful in the treatment or prevention of a number of diseases of a body tissue. The body tissue may be a blood vessel such as coronary artery or a vein, or a lymphatic channel. The body tissue may also be an organ such as the eyes, ears, lungs, kidneys, muscle, myocardium, brain, ovaries, prostate, uterus, placenta and skin. The organs and other tissues may have also been transplanted into the patient; for example, they may have received a transplanted kidney or an artery or vein graft.

A VEGF-D protein of the invention, or an expression vector as defined above may be useful in the treatment of wounds. In a further embodiment, they are useful in the treatment of prevention of ischemia or coronary artery disease. In another embodiment, they are useful in the treatment of neurological disorders.

For therapeutic use, peptides of the invention may be formulated and administered by procedures, and using components, known to those of ordinary skill in the art. The appropriate dosage of the peptide may be chosen by the skilled person having regard to the usual factors such as the condition of the subject to be treated, the potency of the compound, the route of administration etc. Suitable routes of administration include oral, intravenous, intraperitoneal, intramuscular, intranasal and subcutaneous.

The following study illustrates the invention.

Cloning of the Constructs and Virus Generation

The VEGF-D$^{\Delta N \Delta C}$ gene used in this study includes nucleotides 277-603 from the wild-type VEGF-D sequence corresponding amino acids 93-201. The numbering used here is based on the VEGF-D$^{\Delta N \Delta C}$ sequence as presented in FIG. 1. Sequences coding for N-terminal IL-3 signal sequence and Flag-tag and a sequence coding for a C-terminal 6×His are fused to the VEGF-D$^{\Delta N \Delta C}$ sequence. Plasmids encoding mutant VEGF-D$^{\Delta N \Delta C}$ proteins were generated using quick-change site-directed mutagenesis with pEntry-VEGF-D$^{\Delta N \Delta C}$ plasmid as a template. Human VEGF-A$_{121}$ cDNA was cloned into pDonr201 vector (Invitrogen) using BP-reaction. Coding sequences of the Entry clones were then cloned into pBV-boostFG system vectors using LR reaction (Laitinen 2005). Recombinant baculoviruses were generated as previously described.

Protein Expression in Insect Cell Culture and Purification

Recombinant proteins were expressed in recombinant baculovirus (MOI 5) infected High Five cells in shake cultures 72 hours. Proteins were purified from clarified culture mediums using BD Talon Metal Affinity Resin (BD Biosciences Clontech). 3 ml resin was agitated in medium for 2 hours in room temperature and the resin was collected and moved to chromatography columns. Washing was done using 30 ml 50 mM Sodium Phosphate with 300 mM NaCl, pH 7,0. Recombinant proteins were eluted using 50 mM HEPES, 20 mM NaCl, 200 mM imidazole, pH7.4. Proteins were dialyzed against 50 mM HEPES, 20 mM NaCl, pH7.4, to remove imidazole. Protein concentrations were measured using DC protein assay kit (BioRad) using BSA as a standard and the measured protein concentrations were verified by SDS-PAGE. Recombinant human VEGF-A165 was purchased form R&D Systems.

Protein Expression in Mammalian Cells 293T cells were transiently transfected with pBVboostFG system vectors using FugeneHD transfection reagent from Roche according to manufacturer's instructions. Conditioned medium was collected after 52 h-72 h from transfection. The level of VEGF-D proteins in the medium was quantified by Human VEGF-D immunoassay from R&D systems.

SDS-PAGE and Western Blotting

Purified proteins were analyzed by SDS-PAGE in both denaturing and non-denaturing conditions, staining the gels with Silver Snap Stain KitII (Pierce) or Page Blue Protein Staining Solution (Fermentas). Alternatively, proteins were transferred to nitrocellulose membrane and detected using a VEGF-D monoclonal antibody (MAB286, R&D Systems).

In Vitro Studies

Ba/F3-R2 (Achen 1998) and Ba/F3-R3 (Achen 2000) cell survival assays were done by plating 18000 cells per well to 96-well plates and adding recombinant proteins or conditioned medium from transiently transfected 293T cells in serial dilutions. The cell viability was quantified after 48 h. 20 µl Cell Titer Blue Reagent (Promega) was added to each well; plates were incubated two hours at 37° C. Fluorescence was read using Wallac Victor2 1420 Multilabel Counter (Perkin Elmer Biosystems).

RESULTS

Production of recombinant VEGF-$D^{\Delta N \Delta C}$ proteins: The possible intermolecular disulfide bond-forming cysteines (Cys44 and Cys53) and the unpaired cysteine residue (Cys25) of the mature form of VEGF-D, VEGF-$D^{\Delta N \Delta C}$, were each replaced separately by alanine residues. Constructs were named as VEGF-$D^{\Delta N \Delta C}$25A, VEGF-$D^{\Delta N \Delta C}$44A and VEGF-$D^{\Delta N \Delta C}$53A. The recombinant proteins were produced on High Five insect cell line using BVboostFG baculovirus expression system and purified from the culture medium using immobilized metal affinity chromatography. All constructs were successfully expressed and purified as detected by western blotting. However, VEGF-$D^{\Delta N \Delta C}$44A protein was repeatedly lost during following dialysis, probably due to degradation or aggregation and unspecific binding to the dialysis cassette. As also the expression levels of this protein were lower than other VEGF proteins, it may be that this mutation hinders protein folding or reduces stability. Human VEGF-$A_{121}$ recombinant protein was produced and purified similarly for use as a control.

Covalent dimer formation: The ability of VEGF-$D^{\Delta N \Delta C}$, VEGF-$D^{\Delta N \Delta C}$25A and VEGF-$D^{\Delta N \Delta C}$53A to form covalent dimers was evaluated by SDS-PAGE on non-reducing conditions. VEGF-$D^{\Delta N \Delta C}$ was found to be partially a covalent dimer whereas VEGF-$D^{\Delta N \Delta C}$25A formed an increased amount of covalently bound dimers compared to the native form. As expected, covalent dimer formation of VEGF-$D^{\Delta N \Delta C}$53A was hindered.

VEGF-D protein containing the mutation Gly51→Cys or Cys25→Leu; VEGF-D containing the mutations, Arg22→Leu and Cys25→Leu; and VEGF-D containing the mutations Arg22→Ile and Cys25→Leu, all showed increased dimer to monomer ratio compared to VEGF-$D^{\Delta N \Delta C}$. As expected, certain modifications in the VEGF-D dimer interface can clearly alter the multimerization status of the protein.

Activity measurement in vitro: The biological activities of purified VEGF-$D^{\Delta N \Delta C}$, VEGF-$D^{\Delta N \Delta C}$25A and VEGF-$D^{\Delta N \Delta C}$53A were measured using Ba/F3 cell survival assays using cells expressing either VEGFR-2/EpoR or VEGFR-3/EpoR chimeric receptors. In both assays, VEGF-$D^{\Delta N \Delta C}$53A mutant was found to have completely lost its VEGF receptor activation ability, whereas VEGF-$D^{\Delta N \Delta C}$25A mutant had about ten times higher activity compared to native VEGF-$D^{\Delta N \Delta C}$. The proteins purified from insect cell media and conditioned medium from transiently transfected 293T cells were found to have similar activities, showing that the increase in activity of VEGF-$D^{\Delta N \Delta C}$25A mutant is independent of the production system.

To study which amino acid would be most appropriate to substitute Cys25 in VEGF-$D^{\Delta N \Delta C}$, several mutant forms were generated with different amino acids substituting Cys25. The amino acids were chosen to cover different chemical properties. Transient transfection of 293T cells was used to produce conditioned media, and the activities of proteins were measured on cell survival assays with Ba/F3 cells expressing either VEGFR-2/EpoR or VEGFR-3/EpoR chimeric receptor. Each protein was analysed in three different concentrations: 10, 100 and 1000 ng/ml. The mutant forms with hydrophobic amino acids (Leu, Ile, Val) substituting the Cys25 were found to be ones with highest VEGFR-2 and VEGFR-3 dimerization activity. Increased activity compared to native VEGF-$D^{\Delta N \Delta C}$ was also seen with following amino acids substituting Cys25: Ala, Ser, Phe, Trp and Asn. The substitution of the Cys25 with Gly led to inactivation of growth factor.

The results show that the conserved cysteines, forming disulfide bridges in the other members of the VEGF family, are essential for the function of VEGF-$D^{\Delta N \Delta C}$. More importantly, it was also found that removing the unpaired cysteine (Cys25) from the dimer interface of VEGF-$D^{\Delta N \Delta C}$ actually improved the activity of VEGF-$D^{\Delta N \Delta C}$ protein in the sense of vascular endothelial growth factor receptor two and receptor three activation. Therefore, these novel Cys25 mutants of VEGF-$D^{\Delta N \Delta C}$ may prove to be a more effective mediator of therapeutic angiogenesis than its wild-type predecessor, either used as a recombinant protein or administered by gene therapy. For example, an expression vector including a nucleotide sequence encoding a VEGF-D protein of the invention, may be used in gene therapy.

REFERENCE LIST

Achen et al (1998) *Proc. Natl. Acad. Sci. U.S.A* 95, 548-553
Markkanen et al (2005) *Cardiovasc. Res.* 65, 656-664
Laitinen et al (2005) *Nucleic Acids Res.* 33, e42
Airenne et al (2003) *Nucleic Acids Res.* 31, e101
Stacker et al (1999) *J. Biol. Chem.* 274(45): 32127-32136

The invention claimed is:

1. VEGF-D$^{\Delta N \Delta C}$ (SEQ ID NO: 1), wherein the Cys25 residue has been replaced by another amino acid.

2. The protein according to claim 1, wherein the another amino acid is Leu, Ile, Val, Ala, Ser, Phe, Trp or Asn.

3. The protein according to claim 2, wherein the another amino acid is Leu, Ile or Val.

4. The protein according to claim 3, wherein said another amino acid is Leu.

5. The VEGF-D protein according to claim 1, which exists substantially as a dimer.

6. A method for promoting angiogenesis wherein said method comprises administering, to a subject in need of angiogenesis promotion, a modified VEGF-D protein of claim 1.

7. The method, according to claim 6, used to treat ischemia or coronary artery disease by mediating therapeutic angiogenesis.

8. An isolated nucleotide sequence encoding a VEGF-D$^{\Delta N \Delta C}$ (SEQ ID NO: 1) protein wherein the Cys25 residue has been replaced by another amino acid.

* * * * *

SEQUENCE LISTING

<160> NUMBER OF SEQ ID NOS: 6

<210> SEQ ID NO 1
<211> LENGTH: 109
<212> TYPE: PRT
<213> ORGANISM: Artificial Sequence
<220> FEATURE:
<223> OTHER INFORMATION: Fragment -continued

```
<400> SEQUENCE: 1

Phe Tyr Asp Ile Glu Thr Leu Lys Val Ile Asp Glu Glu Trp Gln Arg
1               5                   10                  15

Thr Gln Cys Ser Pro Arg Glu Thr Cys Val Glu Val Ala Ser Glu Leu
            20                  25                  30

Gly Lys Ser Thr Asn Thr Phe Phe Lys Pro Pro Cys Val Asn Val Phe
        35                  40                  45

Arg Cys Gly Gly Cys Cys Asn Glu Glu Ser Leu Ile Cys Met Asn Thr
    50                  55                  60

Ser Thr Ser Tyr Ile Ser Lys Gln Leu Phe Glu Ile Ser Val Pro Leu
65                  70                  75                  80

Thr Ser Val Pro Glu Leu Val Pro Val Lys Val Ala Asn His Thr Gly
                85                  90                  95

Cys Lys Cys Leu Pro Thr Ala Pro Arg His Pro Tyr Ser
            100                 105

<210> SEQ ID NO 2
<211> LENGTH: 95
<212> TYPE: PRT
<213> ORGANISM: Artificial Sequence
<220> FEATURE:
<223> OTHER INFORMATION: Fragment

<400> SEQUENCE: 2

Glu Val Val Lys Phe Met Asp Val Tyr Gln Arg Ser Tyr Cys His Pro
1               5                   10                  15

Ile Glu Thr Leu Val Asp Ile Phe Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45

Cys Asn Asp Glu Gly Leu Glu Cys Val Pro Thr Glu Glu Ser Asn Ile
    50                  55                  60

Thr Met Gln Ile Met Arg Ile Lys Pro His Gln Gly Gln His Ile Gly
65                  70                  75                  80

Glu Met Ser Phe Leu Gln His Asn Lys Cys Glu Cys Arg Pro Lys
                85                  90                  95

<210> SEQ ID NO 3
<211> LENGTH: 94
<212> TYPE: PRT
<213> ORGANISM: Artificial Sequence
<220> FEATURE:
<223> OTHER INFORMATION: Fragment

<400> SEQUENCE: 3

Lys Val Val Ser Trp Ile Asp Val Tyr Thr Arg Ala Thr Cys Gln Pro
1               5                   10                  15

Arg Glu Val Val Val Pro Leu Thr Val Glu Leu Met Gly Thr Val Ala
            20                  25                  30

Lys Gln Leu Val Pro Ser Cys Val Thr Val Gln Arg Cys Gly Gly Cys
        35                  40                  45

Cys Pro Asp Asp Gly Leu Glu Cys Val Pro Thr Gly Gln His Gln Val
    50                  55                  60

Arg Met Gln Ile Leu Met Ile Arg Tyr Pro Ser Ser Gln Leu Gly Glu
65                  70                  75                  80

Met Ser Leu Glu Glu His Ser Gln Cys Glu Cys Arg Pro Lys
                85                  90
```

-continued

```
<210> SEQ ID NO 4
<211> LENGTH: 98
<212> TYPE: PRT
<213> ORGANISM: Artificial Sequence
<220> FEATURE:
<223> OTHER INFORMATION: Fragment

<400> SEQUENCE: 4

Glu Ile Leu Lys Ser Ile Asp Asn Glu Trp Arg Lys Thr Gln Cys Met
1               5                   10                  15

Pro Arg Glu Val Cys Ile Asp Val Gly Lys Glu Phe Gly Val Ala Thr
            20                  25                  30

Asn Thr Phe Phe Lys Pro Pro Cys Val Ser Val Tyr Arg Cys Gly Gly
        35                  40                  45

Cys Cys Asn Ser Glu Gly Leu Gln Cys Met Asn Thr Ser Thr Ser Tyr
    50                  55                  60

Leu Ser Lys Thr Leu Phe Glu Ile Thr Val Pro Leu Ser Gln Gly Pro
65                  70                  75                  80

Lys Pro Val Thr Ile Ser Phe Ala Asn His Thr Ser Cys Arg Cys Met
                85                  90                  95

Ser Lys

<210> SEQ ID NO 5
<211> LENGTH: 98
<212> TYPE: PRT
<213> ORGANISM: Artificial Sequence
<220> FEATURE:
<223> OTHER INFORMATION: Fragment

<400> SEQUENCE: 5

Glu Thr Leu Lys Val Ile Asp Glu Glu Trp Gln Arg Thr Gln Cys Ser
1               5                   10                  15

Pro Arg Glu Thr Cys Val Glu Val Ala Ser Glu Leu Gly Lys Ser Thr
            20                  25                  30

Asn Thr Phe Phe Lys Pro Pro Cys Val Asn Val Phe Arg Cys Gly Gly
        35                  40                  45

Cys Cys Asn Glu Glu Ser Leu Ile Cys Met Asn Thr Ser Thr Ser Tyr
    50                  55                  60

Ile Ser Lys Gln Leu Phe Glu Ile Ser Val Pro Leu Thr Ser Val Pro
65                  70                  75                  80

Glu Leu Val Pro Val Lys Val Ala Asn His Thr Gly Cys Lys Cys Leu
                85                  90                  95

Pro Thr

<210> SEQ ID NO 6
<211> LENGTH: 95
<212> TYPE: PRT
<213> ORGANISM: Artificial Sequence
<220> FEATURE:
<223> OTHER INFORMATION: Fragment

<400> SEQUENCE: 6

Glu Val Val Pro Phe Gln Glu Val Trp Gly Arg Ser Tyr Cys Arg Ala
1               5                   10                  15

Leu Glu Arg Leu Val Asp Val Val Ser Glu Tyr Pro Ser Glu Val Glu
            20                  25                  30

His Met Phe Ser Pro Ser Cys Val Ser Leu Leu Arg Cys Thr Gly Cys
        35                  40                  45

Cys Gly Asp Glu Asn Leu His Cys Val Pro Val Glu Thr Ala Asn Val
    50                  55                  60
```

-continued

```
Thr Met Gln Leu Leu Lys Ile Arg Ser Gly Asp Arg Pro Ser Tyr Val
65                  70                  75                  80

Glu Leu Thr Phe Ser Gln His Val Arg Cys Glu Cys Arg Pro Leu
                85                  90                  95
```